United States Patent [19]

Ochs

[11] Patent Number: 4,461,301

[45] Date of Patent: Jul. 24, 1984

[54] SELF ADJUSTING BIO-FEEDBACK METHOD AND APPARATUS

[75] Inventor: Leonard A. Ochs, Schenectady, N.Y.

[73] Assignee: Self Regulation Systems, Inc., Redmond, Wash.

[21] Appl. No.: 311,631

[22] Filed: Oct. 15, 1981

[51] Int. Cl.³ .............................................. A61B 5/00
[52] U.S. Cl. .................................... 128/630; 128/732; 128/733; 128/734; 128/736; 128/905
[58] Field of Search ................ 128/731, 732, 733, 905

[56] References Cited

U.S. PATENT DOCUMENTS

| | | | |
|---|---|---|---|
| 3,799,146 | 3/1974 | John et al. | 128/731 |
| 3,916,876 | 11/1975 | Freeman | 128/733 |
| 4,170,225 | 10/1979 | Criglar et al. | 128/732 |

OTHER PUBLICATIONS

Zicker et al., "IEEE Transactions on Biomedical Engineering," vol. 27, No. 9, Sep. 1980, pp. 509–515.

Primary Examiner—William E. Kamm
Attorney, Agent, or Firm—Paul I. Edelson

[57] ABSTRACT

A bio-feedback method for training persons in the self-regulation of physiological functions by means of displaying to the person a continuous representation of a value of such physiological functions upon, and together with, a metric which is continuously and automatically variable as a function of such values and the rate of change of such values so as to provide to the person a display in which changes in the physiological function are highly resolvable and therefore easily noticed, and apparatus for practicing such method and disclosed. Means are also optionally provided additionally displaying a target or goal to which the person is to attempt to direct the value of the physiological function; the target is automatically adjusted as a function of the value of the physiological function in such manner that it appears that the target is attainable, but is readjusted to prevent actual attainment of the target. If desired, the target may used without the automatically adjusted metric. In practicing this invention, a physiological function is detected and digitized into a stream of digital signals representing a value of the physiological function over time. Statistical functions of the stream of digital signals are determined to establish the optimal metric and target for use with the physiologic data detected from the person at any point in time, and a simultaneous display of the values of the physiologic function and either the metric, the target, or both, is generated.

7 Claims, 6 Drawing Figures

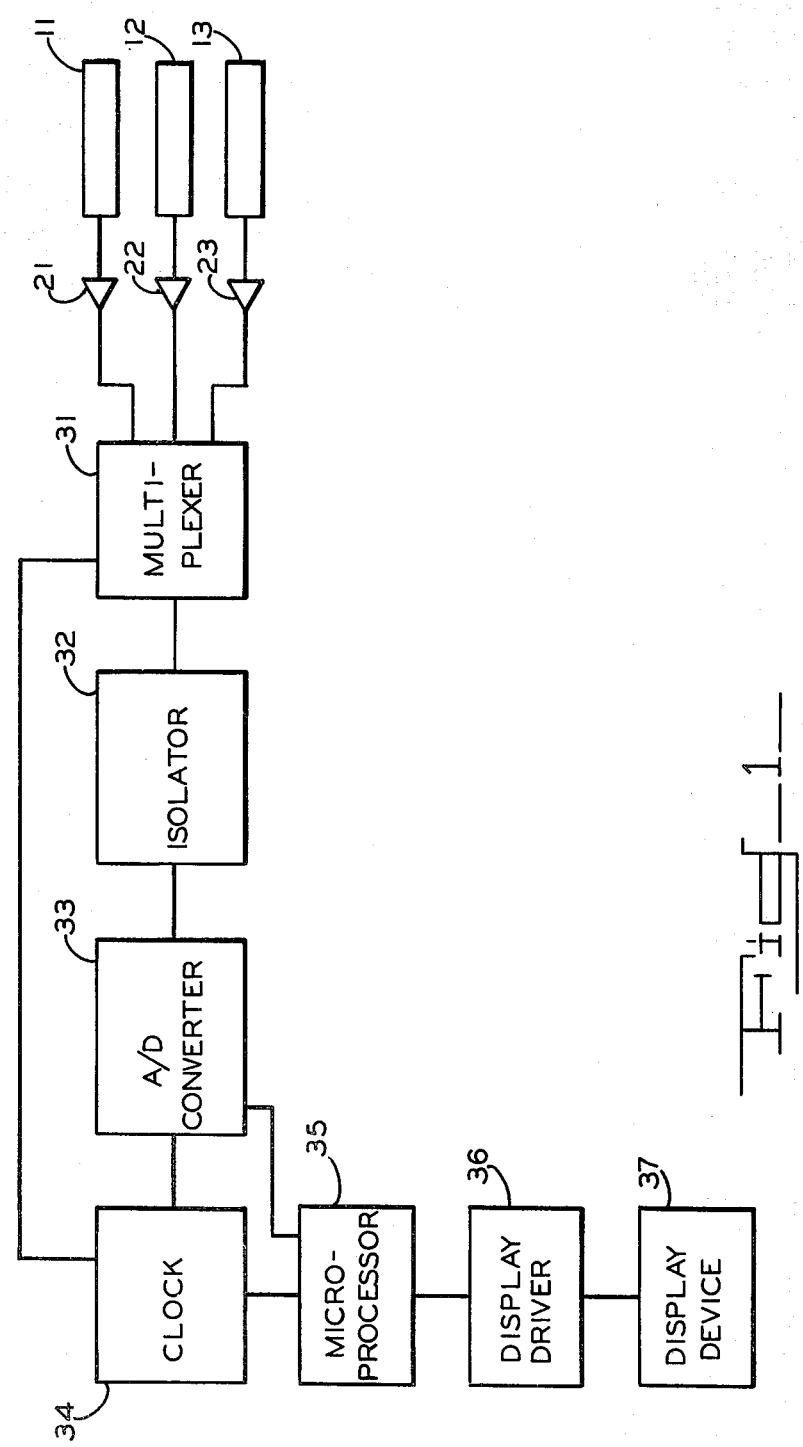

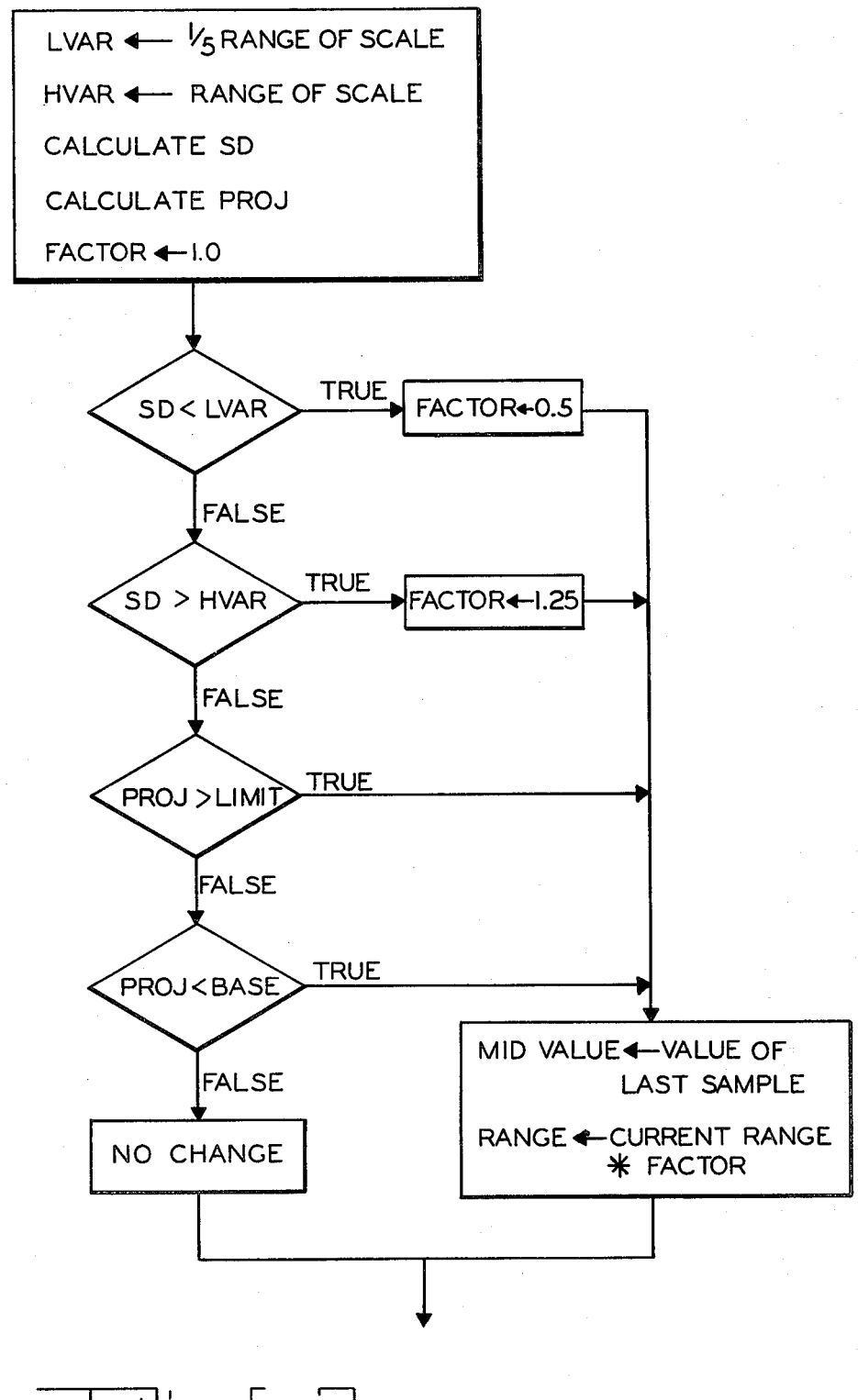

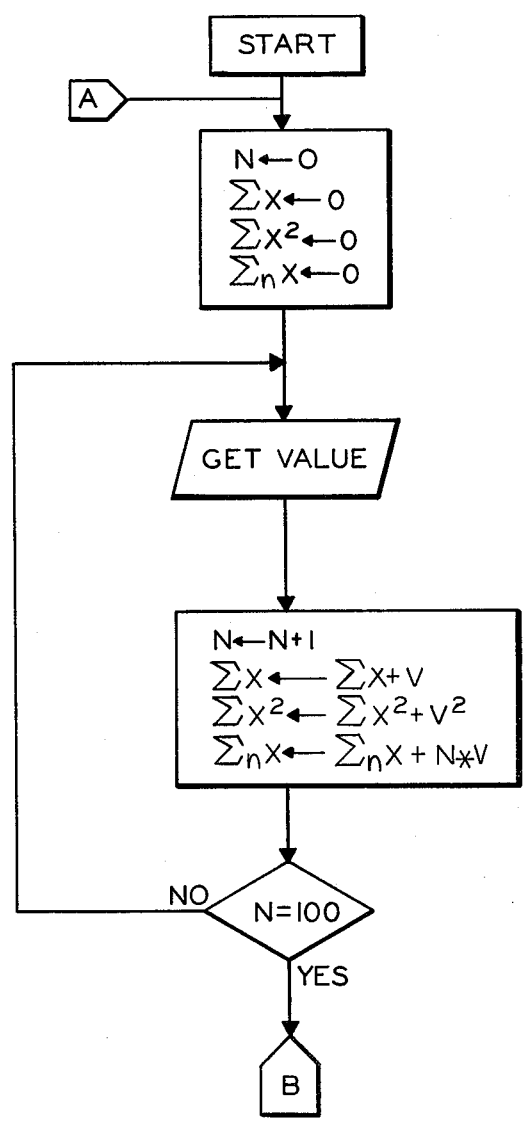
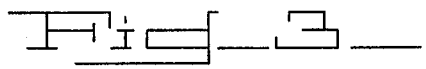

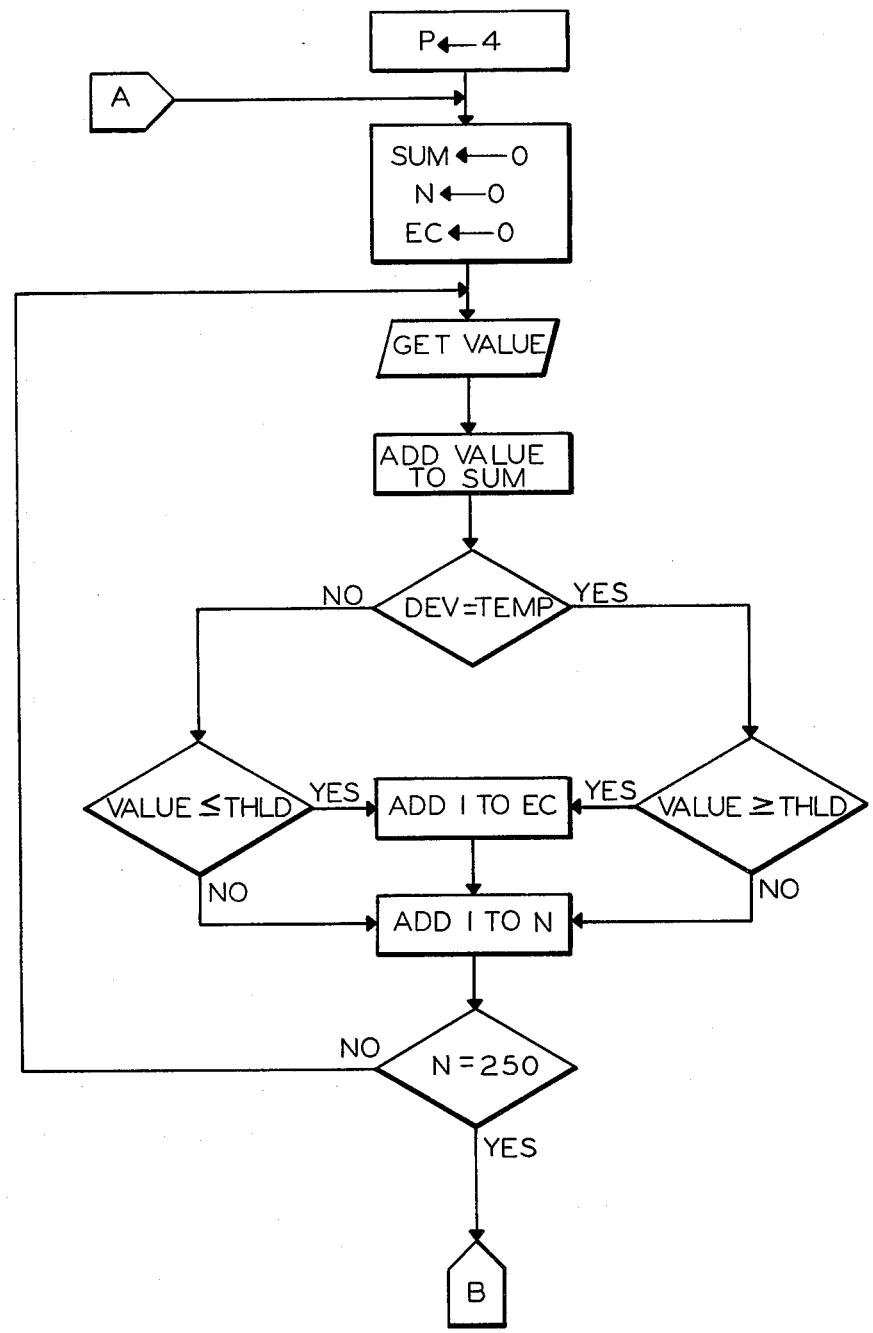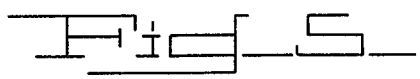

SELF ADJUSTING BIO-FEEDBACK METHOD AND APPARATUS

BACKGROUND OF THE INVENTION

This invention relates to bio-feedback. More particularly this invention relates to method and apparatus for displaying data related to biological functions of a subject to the subject in such form that the subject can learn to interact with the display to control the biological functions, and in which the display is adjusted to enhance the ability of the subject to interact with the display as the values of the physiologic functions being monitored vary.

Bio-feedback as practiced in the prior art involves the display to a subject of signal values related to physiologic functions by means of audible tones, meter readings, and the like. It has been found that the magnitude of variations of values of physiologic functions, and the rates at which such values change with varying subjects at differing levels of capability in bio-feedback control are such that either the display device will be insufficiently sensitive to allow the subject to discern minor changes in the values of a physiologic function, or will be of such limited range that data will go "off scale", or otherwise beyond the display capabilities of the display device. The prior art has attempted to deal with this situation by compressing data by the use of logarithmically responsive display devices, or by the use of a plurality of fixed, discrete, manually switchable display ranges. The use of a logarithmic scale is a limited solution to the problem, because, even with compression, a fixed finite scale is employed in which the possibility of an off scale value still exists. The use of logarithmic scales also presents the disadvantage that, in the compressed area of the scale, resolution is lost. Manual range switching has the disadvantages of requiring the continuous attention of an operator, providing, upon range switching, a drastic, arbitrary, change of display indication, which may momentarily confuse the subject until he realizes that a range change has taken place, and still only provide a small number of available ranges in practical systems so that displays can not be fully optimized for subject/display interaction purposes.

It is, accordingly, an object of this invention to provide bio-feedback method and apparatus in which the display of values of physiologic data from the subject is perceptually optimized to facilitate the interaction between the subject and the display.

It is another object of this invention to accomplish such perceptual optimization by continuously adjusting the scale of the display as functions of the values of the physiologic data and rate of change of such values.

Another object of the invention is to provide a display of a metric simultaneously with the display of the values of the physiologic data.

Another object is to change the display of of the metric coincidentially with a change of range scale to reduce confusion in the subject by immediately indicating the display adjustment to him.

It is another object of this invention to provide for a very large number of available display scale ranges, determined and displayed automatically solely from the physiologic data provided by the subject.

It is another object of this invention to provide for the simultaneous display of values of physiologic data from the subject and a target value toward which the subject is to attempt to direct his physiologic response value.

It is another object of this invention to provide for the continuous modification of the target value, automatically, as a function of the values of the physiologic data from the subject.

Briefly, and in accordance with one embodiment of this invention, a sensor detects a physiologic function of a subject and provides an electrical signal related thereto. The signal is digitized in a converter into a stream of digital signals corresponding to the values of the biological signal over time. A plurality of digital signals are processed for display to the subject, and statistical functions are determined from such plurality of digital signals to determine the optimum scaling of the display, and the appropriate target value to be displayed. The display device is driven to display the appropriate target or the metric of the optimal scale range, or both, simultaneously with the display of values of the physiologic functions provided by the subject. The statisical functions are continuously redetermined, and the display is modified solely responsively to the characteristics of the digitized data stream from the subject.

The novel features of this invention sought to be patented are set forth with particularity in the appended claims. The invention, together with further objects and advantages thereof, may be understood from a reading of the specification and appended claims in view of the accompanying drawings in which:

FIG. 1 a system block diagram in accordance with an embodiment of this invention.

FIG. 2 is a flow chart illustrating the determination of statistical functions of digitized biological data for establishing optimized display range scales for such data FIGS. 3 and 4 are more detailed flow charts of the flow in accordance with one embodiment of this invention. chart of FIG. 2.

FIGS. 5 and 6 are a flow chart for determining a statistical function of digitized biologic data for optimizing a target display in accordance with one embodiment of this invention.

Figure 4:
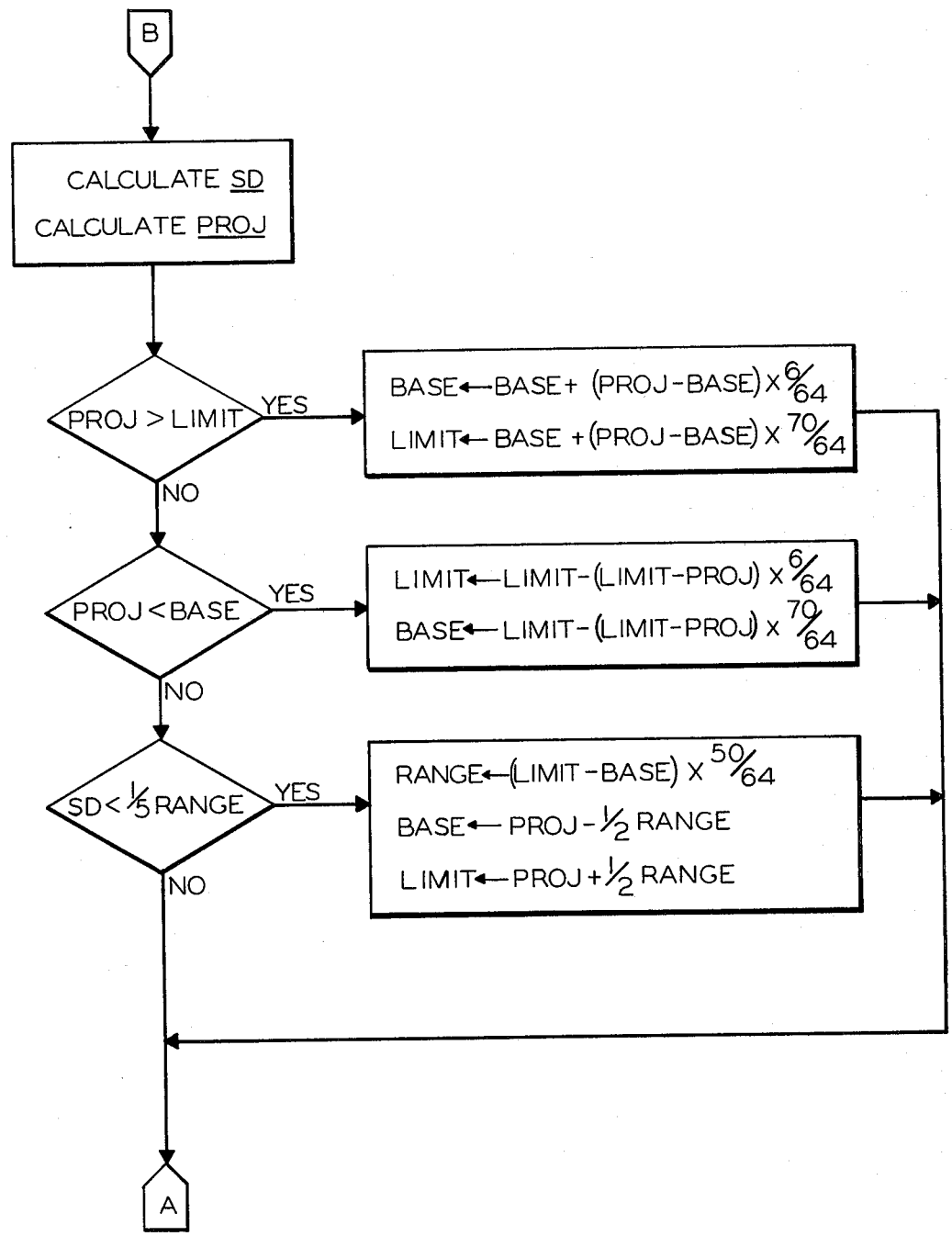

A block diagram of a system for practicing this invention is shown in FIG. 1 and comprises a sensor 11 for detecting a physiologic parameter from a subject and providing an electrical signal proportional to the parameter, and may be a temperature sensor, a skin conductance probe, a myographic potential detector, an encephalographic pick up, or any other such bio-data probe as is known in the art. In accordance with one embodiment of this invention, the system is also provided with additional such probes, 12 and 13, for detecting different biological functions. The outputs of the probes are feed to appropriate preamplifiers, 21, 22, and 23, respectively for processing appropriate to the nature of the probe. If appropriate to the nature of the signal provided by its associated probe, other processing functions, such as filtering, may be provided in elements 21, 22, and 23, as is known in the art. Physiologic signals from a plurality of probes are received by multiplexer 31 which is driven by clock 34, and which provides a multiplex output to isolator 32, which in turn feeds an analog to digital converter 33, which is also driven by clock 34. Converter 33 provides a stream of digitized values of physiologic parameters to micro-processor 35. Micro-processor 35 accumulates digitzed values and provides an output to display driver 36 which in turn drives display device 37, which is preferably a cathoderay tube display device, and may, with an appropriate display driver 36, be a conventional television set, to provide for a display on display device 37 of the values of the physiologic parameters. Micro-processor 35 also determines the values of statistical functions of successive pluralities of digitized signals, and from such statistical functions determines the optimum characteristics for display scaling and for targeting and provides outputs to display driver 36 to cause display 37 to display the physiologic data values over a display range optimized to the instantaneous values of the data and the instantaneous rate of change of the data, to display a range scale with a metric thereon, and to display a target value toward which the subject will attempt to direct his physiologic response.

It should be understood that the immediately foregoing explanation describes the performance of a number of functions in combination but this invention is not so limited; a subset of the functions described is also within the scope of this invention. For example, either the targeting function or the automatic scaling function may be performed alone, and the system of this invention may be employed with only a single sensor for displaying the value of only one physiologic parameter. In the event that a single sensor is used, multiplexer 31 would not be required.

FIGS. 2 through 4 illustrate the determination of one particular statistical function of a particular number of digitized data words useful in optimizing display scaling in accordance with one embodiment of this invention. It should be understood that neither the size of the statistical sample, nor the particular statistical function illustrated in FIGS. 2 and 3 and discussed hereinbelow are limitations of this invention, but are set forth herein as an illustrative example of an embodiment which has been reduced to practice and has provided satisfactory results.

With reference to FIGS. 2, 3, and 4, optimum display scaling may be performed in accordance with this invention by testing, after every 100 samples of digitized data, to determine whether or not a scale change is necessary. First, two values are computed: the standard deviation (SD) of the last 100 samples and the projection (proj) or expected magnitude half way through the next set of 100 samples. These two values each are used for separate determinations. The standard deviation is used to determine if the size of the scale need be changed. If the SD is deemed low than the scale should be decreased in size. Likewise if it is deemed high, the scale should be increased. The projection is used to determine if the placement of the scale need be changed. For example, if the physiologic parameter is temperature, and if the scale ranges from 80 to 90 degrees, and the projection suggests that the temperature is decreasing below 80 degrees, the scale whose size is 10 degrees should be moved downward to accomodate the projected magnitude. At not time is the base allowed to go below zero, the limit above the maximum possible magnitude, or the range less than one unit.

Similarly to the discussion of FIGS. 2 through 4 hereinabove, FIGS. 5 and 6, and the following explanation thereof, constitute an illustrative example of one embodiment of targeting successfully reduced to practice in accordance with this invention, and do not constitute a limitation of this invention with respect to particular functions or sample sizes.

Figure 6:
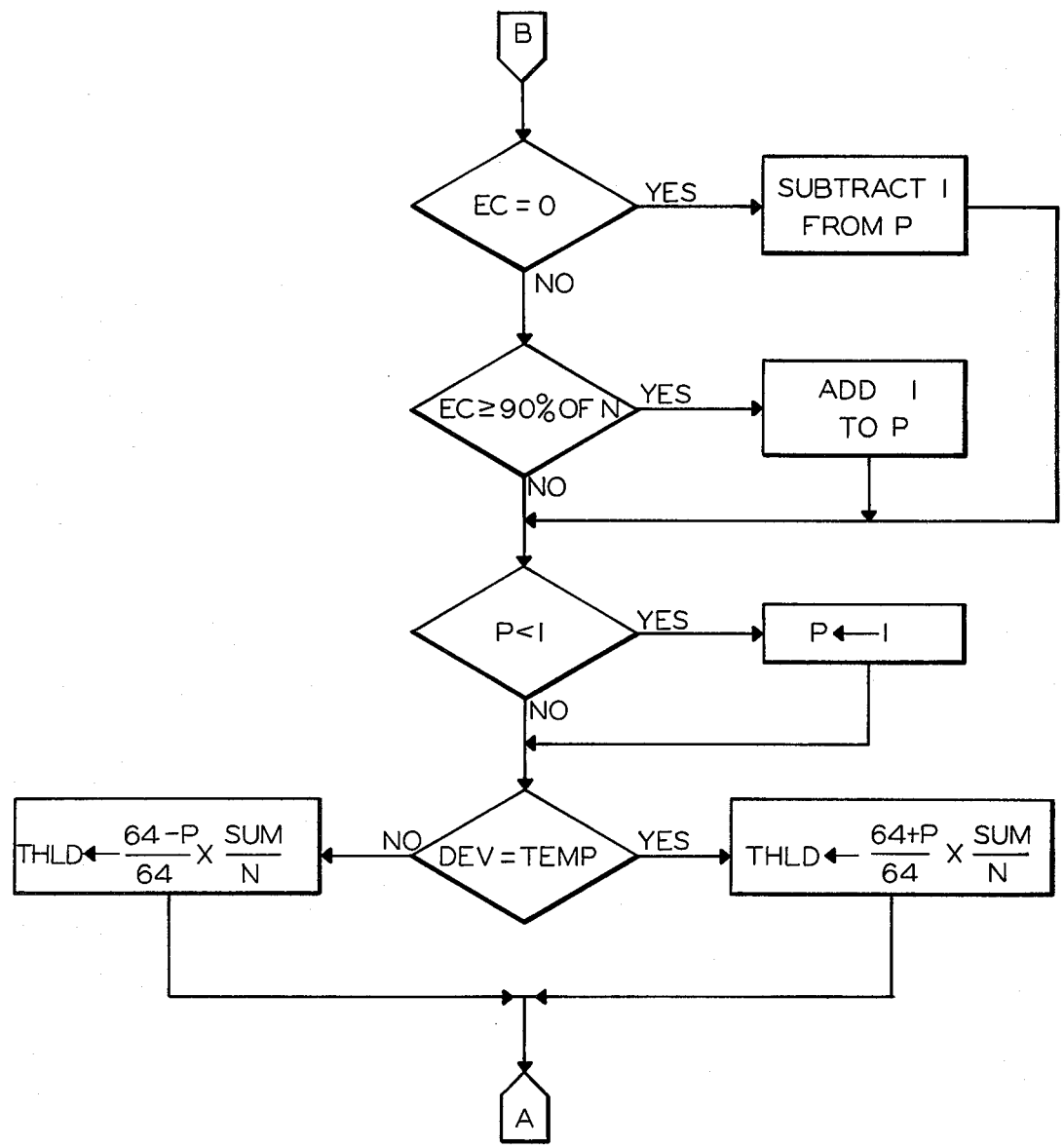

Referring to FIGS. 5 and 6, the target is a function of the mean of the incoming data. It is always set at some value beyond the mean so as to provide a continual goal to strive for. If the target becomes too easy to reach, it is moved even further away from the mean. If it becomes too hard to reach, it is moved closer to the mean.

The decision to move the target in accordance with the illustrated embodiment occurs every 250 digitized data values. A sum of those values is maintained so that their mean can be calculated. Also a count is kept to indicate how many of those values exceeded the target. If this count is zero after 250 values, the target is unreachable and needs to be moved closer to the mean. If the count is more than 90% of 250, the target is considered too easy to reach and is moved farther away from the mean. At no point is the target allowed to come within 2 percent of the mean.

In FIGS. 5 and 6,

THLD is the current value of the target;

N is the number of values taken in;

SUM is the sum of the values;

EC is the count of the values that exceeded THLD; and

P indicates how far from the mean THLD is to be set, in 64ths. For example if $P=1$, then THLD will be set at a value $1/64 \times$ mean beyond the mean. If the parameter is temperature and mean$=85$ then THLD$=85+1/64 \times 85$ or 86.33. If the parameter is EMG and mean$=8.5$ then THLD$=8.5-1/64 \times 8.5$ or 8.37.

The actual percentage that the threshold is set beyond the mean depends on P as such:

| P | % or p/64 × 100 |
|---|---|
| 1 | 1.6 |
| 2 | 3.1 |
| 3 | 4.7 |
| 4 | 6.3 |
| 5 | 7.8 |
| : | : |

While this invention has been described with reference to particular embodiments and examples, other variations and modifications will occur to those skilled in the art in view of the above teachings. Accordingly, it should be understood that within the scope of appended claims, the invention may be practiced otherwis than specifically described.

The invention claimed is:

1. A method of teaching self-regulation to a human subject of said subjects various physiological functions comprising the steps of;
   (a) detecting a signal from said subject of a physiological function sought to be regulated
   (b) digitizing said signal to provide a plurality of digitized signals overtime
   (c) electronically deterining a plurality of values, each value functionally related to a number of said digitized signals
   (d) automatically determining a first statistical function of said digitized signals indicating whether said subject could adequately resolve the display of said values within scaling limits extending from an upper limit to a lower limit of a metric
   (e) determining second statistical function of said digitized signals indicating whether said values will continue to fall within said scaling limits of said metric (f) determining said scaling limits of said metric as a function of said first statistical function said second statistical function; and (g) displaying simultaneously said metric, its scaling limits, and said values to induce said subject to control said physiological function.

2. The method of claim 1 including additionally the step of setting initial values of said upper and lower scaling limits.

3. The method of claim 1 wherein said step of determining said scaling limits more particularly comprises:

establishing the difference between said upper limit and said lower limit as a function of said first statistical function; and establishing the magnitudes of said upper and lower limits as a function of said second statistical function.

4. The method of claim 3 wherein said step of determining a first statistical function more particularly comprises computing the standard deviation of said number of said digitized signals included in the determination of each of said values.

5. The method of claim 5 wherein said step of determining a second statistical function more particularly comprises computing from said number of digitized signals included in the determination of each of said values the expected magnitude of said digitized signals included in the determination of the next value of said plurality of values.

6. The method of claim 1 including additionally the steps of:

automatically determining a third statistical function of said digitized signals;

generating from said third statistical function a target value toward which said subject is to attempt to direct said values by controlling said physiological function; and displaying simultaneously said metric, its scaling limits, said values, and said target.

7. The method of claim 6 further including the step of continuously recomputing said third statistical function for each of a second number of said digitized signals whereby said display of said target is moved to continuously motivate said subject in the task of controlling said physiological function.

* * * * *